(12) United States Patent
New

(10) Patent No.: US 9,096,650 B2
(45) Date of Patent: Aug. 4, 2015

(54) CYCLIC OLIGOPEPTIDES FOR BINDING TO A TARGET LIGAND

(75) Inventor: Roger New, London (GB)

(73) Assignee: LEXCICON LIMITED, Jersey (GB)

(*) Notice: Subject to any disclaimer, the term of this patent is extended or adjusted under 35 U.S.C. 154(b) by 1719 days.

(21) Appl. No.: 12/442,172

(22) PCT Filed: Sep. 20, 2007

(86) PCT No.: PCT/GB2007/003592
§ 371 (c)(1),
(2), (4) Date: May 12, 2009

(87) PCT Pub. No.: WO2008/035093
PCT Pub. Date: Mar. 27, 2008

(65) Prior Publication Data
US 2010/0022448 A1 Jan. 28, 2010

(30) Foreign Application Priority Data

Sep. 20, 2006 (GB) .................................. 0618512.8
Apr. 19, 2007 (GB) .................................. 0707626.8

(51) Int. Cl.
*C07K 7/64* (2006.01)
*A61K 38/00* (2006.01)

(52) U.S. Cl.
CPC .. *C07K 7/64* (2013.01); *A61K 38/00* (2013.01)

(58) Field of Classification Search
None
See application file for complete search history.

(56) References Cited

FOREIGN PATENT DOCUMENTS

| JP | 2000143698 | 5/2000 |
| WO | WO01/01140 | 1/2001 |
| WO | WO2006/043933 | 4/2006 |

OTHER PUBLICATIONS

Schreier et al. "Surface active drugs: self-association and interaction with membranes and surfactants. Physicochemical and biological aspects," Biochimica et Biophysica Acta 1508 (2000) 210-234.*
Gura "System for Identifying New Drugs are Often Faulty," Science, Nov. 1997, vol. 278, pp. 1041-1042.*
Kamb "What's wrong with our cancer models?" Nature Reviews, Feb. 2005, vol. 4, 161-165.*
Davidson "Autoimmune Diseases" N Engl J Med, Aug. 2001, vol. 345, 340-350.*
Jones "Biologic therapy in Crohn's disease: state of the art," Current Opinion in Gastroenterology, 2008, 24:475-481.*
Nishino, N., et al., "Lipophilic Cyclic Hexapeptide for Calcium Ion-Selective-Electrode," Chem. Lett. 1992;21(4):665-668.
Benito, J. M., et al., "Bicyclic Organo-Peptides as Selective Carbohydrate Receptors: Design, Solid-phase Synthesis, and on-bead Bdinging Capability," QSAR Comb. Sci. 2004;23:117-129.
Catalioto, R-M., et al., "Men 11420 (Nepadutant), a novel glycosylated bicyclic peptide tachykinen NK2 receptor antagonist," British H. Pharmacol. 1998;123:81-91.
Crusi, E., et al., "Peptide Ionophores: Synthesis and Cation-Binding Properties of a Bicyclic Peptide Containing Glycine and Lysine Residues," Peptide Res. 1995;8(2):62-69.
Deber, C. M., et al., "Cation-Binding Cyclic Peptides with Lipophilic Tails," Bipolymers 1979;18(10):2375-2396.
Jaulent, A. M., et al., "Design, synthesis and analysis of novel bicyclic and bifunctional protease inhibitors," Protein Eng Des. Selec. 2004;17(9):681-687.
Mihara, H., et al., "Synthesis of [L-α-Aminomyristic Acid$^{3,3}$]gramicidin S and Its Interaction with Phospholipid Bilayer," Bull. Chem. Soc. Jpn. 1992;65:228-233.
Nishino, N., et al., "Cyclic Octapeptides Containing Alpha-Aminofatty Acids as Calcium Ionophores," Peptide Chem. 1986; Protein Research Foundation, Osaka, XP009096279, pp. 101-104.
Patacchini, R., et al., "Effect of several bicyclic peptide and cyclic pseudopeptide tachykinen NK$_2$ receptor antagonists in the human isolated ileum and colon," Neuropeptides 1997;31(1):71-77.
Roller, P. P., et al., "Bicyclic Peptide Inhibitors of an Epithelial Cell-Derived Transmembrane Protease, Matriptase," Proceedings of the International and the American Peptide Symposium, Jun. 9, 2001, pp. 561-562.
Sasaki, H., et al., "Binding and Detection of Organic Molecules by Cyclic Peptides with Long Alkyl Chains and Fluorescent Probes," Peptide Sci. 1998;35:421-424.
Sun, Y., et al., "A Thioester Ligation Approach to Amphopathic Bicyclic Peptide Library," Org. Lett. 2001;3(11):1681-1684.
Zanotti, G., et al., "Syntheses of Monocyclic and Bicyclic Peptides of Tryptathionine and Glycine," Int. J., Peptide Protein Res. 1978;12:204-216.
International Search Report and Written Opinion of the International Searching Authority for PCT Patent App. No. PCT/GB2007/003592 (Aug. 13, 2008).

* cited by examiner

*Primary Examiner* — Christina Bradley
(74) *Attorney, Agent, or Firm* — Shelly Guest Cermak; Cermak Nakajima & McGowan LLP

(57) ABSTRACT

An internally-constrained cyclic oligopeptide comprising a ring of at least six amino acids for specifically binding to a target ligand, wherein the ring comprises a plurality of amino acid domains, each domain comprising at least two epitope-forming amino acids, and two or more associating functional groups positioned so that they form one or more intra-cyclic associations; whereby the cyclic oligopeptide is constrained in a single conformation so that the epitope-forming amino acids form an epitope in each domain, each epitope being capable of specifically binding to a target ligand.

7 Claims, No Drawings

CYCLIC OLIGOPEPTIDES FOR BINDING TO A TARGET LIGAND

This application is a U.S. national phase filing under 35 U.S.C. §371 of PCT Application No. PCT/GB2007/-3592, filed Sep. 20, 2007, and claims priority thereto under 35 U.S.C. §119 to British patent application nos. 0618512.8, filed Sep. 20, 2006, and 0707626.8, filed Apr. 19, 2007, the entireties of which are incorporated by reference herein.

The present invention relates to an internally constrained cyclic oligopeptide, a pharmaceutical composition comprising such an oligopeptide, uses of such an oligopeptide and pharmaceutical composition in medicine and a method for producing such an oligopeptide.

BACKGROUND OF THE INVENTION

Protein receptors are known normally to bind to their target ligands via epitopes, combinations of amino acids, which constitute a small proportion of the total protein molecule.

Protein receptors on the surface of cells are often triggered to produce a signal within the cell as a result of binding to other proteins, termed protein ligands. The portion of the ligand which interacts with the receptor is termed an epitope, and usually constitutes a combination of a small number of amino acids in close proximity with each other, held on the backbone of the peptide chain. Examples of epitopes are those structures on the surface of proteins which interact with antibodies or T-cell receptors, but in fact any structure on the surface of a protein which is recognised specifically by another can fall within the definition of an epitope. Because the binding of a protein receptor with an epitope can be an important step in the etiology of a disease, or conversely, in the treatment of a disease condition, the identification of functional groups which form epitopes is a potentially fruitful avenue for development of new drugs, where the drug is an agent comprising an epitope which binds to the receptor.

Two challenges exist which hinder this approach to new drug development. One is the identification of epitopes which can be employed as drug molecules to bind to appropriate receptors in order to treat a disease. The second challenge is to design molecules which can hold and present the combination of amino acids forming the epitope such that a strong binding interaction with a cell receptor can be achieved.

Methods are known for identifying combination of amino acids which can form epitopes. In traditional combinatorial chemistry, the identification of the most favourable sequence for binding to a specific receptor must be carried out by synthesis of hundreds of possible combinations of different groups such as amino acids, in different orders, each one having to be tested for efficacy. This process is time-consuming, expensive and is limited by the nature of the chemistry which can be carried out in linking the different components together.

WO 01/01140 provides an improved way of identifying epitopes. A composition is provided for interacting with a ligand. The composition comprises a non-covalent assembly of a plurality of distinct conjugates each conjugate comprising a head group and a tail group. The tail groups of the conjugates form a hydrophobic aggregation and the conjugates have freedom of motion with respect to each other within the assembly so that, in the presence of a ligand, at least two of the head groups are appropriately positioned to form an epitope capable of interacting with the ligand more strongly than each of the head groups individually. The plurality of conjugates which has the desired biological activity may be identified by selecting a set of conjugates with an array of head groups, forming a non-covalent association therefrom, in which the tail groups aggregate hydrophobically and in which the conjugates exhibit freedom of motion with respect to one another and assaying for sufficient interaction between the non-covalent association and the ligand. This process may be repeated with a modified array of head groups in order to find sufficient interaction between the non-covalent association and the ligand. This process allows for the identification of the most favourable sequence for binding to a specific receptor by relying on the proximity of the head groups to provide association-derived epitopes without the need for the synthesis of hundreds of possible combinations of different groups using traditional combinatorial chemistry. The method simply relies upon proximity of the head groups to provide association-derived epitopes. Once a set of conjugates has been synthesised, no further synthetic chemistry is required, only simple mixing of the conjugates to form the different probes by non-covalent association.

Whilst this new composition and method have been successful for identifying the functional groups which form the epitope and bind to the target ligand, there is still a requirement to provide improved compositions which are capable of forming the desired epitope and interacting with improved stability and specificity with the target ligand to produce a biological response.

Attempts to produce an analogous peptide to the epitope constructed solely of the amino acids comprising the binding site often fail because these peptides do not possess the same biological activity as the protein receptor.

Where the binding site of a protein is constructed of oligopeptides from different, non-contiguous parts of a protein chain, attempts to reconstruct the binding site by mixing isolated oligopeptides in free solution does not result in the active binding site.

Accordingly, the present invention aims to provide improved oligopeptides which are capable of forming a desired epitope, which can interact with improved stability and specificity with the target ligand to produce a biological response.

SUMMARY OF THE INVENTION

The invention provides a cyclic oligopeptide comprising a ring of at least six amino acids for specifically binding to a target ligand, wherein the ring comprises a plurality of amino acid domains, each domain comprising at least two epitope-forming amino acids, and two or more associating functional groups positioned so that they form one or more intra-cyclic associations; whereby the cyclic oligopeptide is constrained in a single conformation so that the epitope-forming amino acids form an epitope in each domain, each epitope being capable of specifically binding to a target ligand.

Cyclic peptides are known in the art to have a conformation which is more restricted than linear oligopeptides. The freedom of movement of the ends of the peptide is limited in a cyclic peptide because they have been anchored together chemically. However, cyclic peptides still have a considerable degree of flexibility which makes them unsuitable for participating in stable binding interactions with a target ligand.

By constructing cyclic oligopeptides with two or more associating functional groups positioned so that they form one or more intra-cyclic associations, the cyclic oligopeptide is constrained internally in a single conformation. This allows the epitope-forming amino acids in each domain to bind specifically to a target ligand with more stability and specificity than hitherto available. The epitope-forming amino acids are able to form a stable epitope for interacting with a ligand to induce a biological response. Because the epitope is stably formed there is improved interaction with the target ligand.

US 2005/0107289 discloses anti-microbial agents and compositions that include cyclic peptides having an amino acid sequence of alternating D- and L-α-amino acids or β-amino acids. This document further discloses that the cyclic peptides are believed to self-assemble into supramolecular structures within or by association with microbial membranes. Such supramolecular structures can be, for example, nanotubes. Each nanotube has a pore in the centre of the tube that is surrounded by a series of peptide backbones of the stacked cyclic peptides. Ions and small molecules can travel through the pores of the nanotubes.

US 2005/0107289 does not disclose that the cyclic peptides comprise epitope-forming amino acids which form epitopes capable of specifically binding to a target ligand. US 2005/0107289 also does not disclose that the cyclic peptides are constrained by intra-cyclic associations in order to allow the formation of such epitopes.

G. Abbenante et al. "*Conformational Control by Thiazole and Oxazoline Rings in Cyclic Octapeptides of Marine Origin. Novel Macrocyclic Chair and Boat Conformations; J. Am. Chem. Soc.* 1996, 118, 10384-10388 discloses the adaptation of amino acid building blocks (Thr, Cys) as conformational ring constraints (oxazoline, thiazole) to regulate three-dimensional structures and reactivities of marine macrocycles. Cyclic octapeptide 1, c[Ile-Thr-D-Val-Cys-Ile-Thr-D-Val-Cyc-] is very flexible, adopting many low energy structures. This cyclic octapeptide does not have any intra-cyclic associations and is not constrained in a single conformation to form a plurality of epitopes.

G. Abbenante et al. "*Conformational Control by Thiazole and Oxazoline Rings in Cyclic Octapeptides of Marine Origin. Novel Macrocyclic Chair and Boat Conformations; J. Am. Chem. Soc.* 1996, 118, 10384-10388 also discloses cyclic peptide 2, c[Ile-Thr-D-(Val)Thz-Ile-Thr-D-(Val)Thz-], which showed a single pseudochair conformation in solution. Cyclic peptide 7, c[(Ile)Oxn-D-(Val)-Thz-(Ile)Oxn-D-(Val)Thz-], was synthesized and produced a highly constrained pseudoboat or saddle-shaped macrocycle. Cyclic octapeptide 8, produced by acid hydrolysis of 7, showed a boat conformation with greater flexibility. These cyclic octapeptides are constrained to a degree by the presence of the oxazolines and/or thiazoles but they do not form a plurality of epitopes.

R. M. Cusack et al., *Conformations of cyclic octapeptides and the influence of heterocyclic ring constraints upon calcium binding; J. Chem. Soc., Perkin Trans.* 2, 2000, 323-331 discloses four cyclic octapeptides that differ in the number of heterocyclic thiazole and oxazoline ring constraints. Peptides 1, 2 and 3 adopted different shapes in solution. These cyclic octapeptides are constrained to a degree by the presence of the oxazolines and/or thiazoles but they do not form a plurality of epitopes.

R. M Cusack et al., *Conformations of cyclic octapeptides and the influence of heterocyclic ring constraints upon calcium binding; J. Chem. Soc., Perkin Trans.* 2, 2000, 323-331 also discloses peptide 4 lacking oxazoline and thiazole rings and molecular modelling showed that such cyclic peptides lacking any constraints apart from hydrogen bonding are very flexible and can potentially adopt a myriad of conformations in solution. Peptide 4 does not have any intra-cyclic associations and is not constrained in a single conformation to form a plurality of epitopes.

The cyclic oligopeptide of the present invention will now be described in further detail.

The cyclic oligopeptide comprises a ring of at least six amino acids, wherein the ring comprises a plurality of amino acid domains, wherein each domain comprising at least two epitope-forming amino acids, and two or more associating functional groups.

In one embodiment, the cyclic oligopeptide consists of a ring of six amino acids, wherein the ring consists of two amino acid domains, each domain consisting of two epitope-forming amino acids, and two associating functional groups. In a preferred embodiment, the cyclic oligopeptide consists of a ring of eight amino acids, wherein the ring consists of two amino acid domains, each domain consisting of three epitope-forming amino acids, and two associating functional groups.

In an alternative embodiment, the cyclic oligopeptide comprises a ring of more than eight amino acids. In this embodiment, preferably the ring comprises three associating functional groups, which form intra-cyclic associations to produce three amino acid domains, each domain comprising three epitope-forming amino acids.

The amino acids employed in the cyclic oligopeptide can be any of the natural amino acids, substituted derivatives, analogues, and D-forms thereof.

In a preferred embodiment of the present invention there are three epitope-forming amino acids which have alternating stereochemical configurations, i.e. either L-D-L or D-L-D. This is particularly advantageous because it permits the side chains of the epitope-forming amino acids to be orientated in a planar configuration, all facing in the same direction. This allows the epitope-forming amino acids to be in close proximity with each other to form the epitope.

In an alternative embodiment, the cyclic oligopeptide consists of a ring of ten amino acids wherein the ring consists of two amino acid domains, each domain consisting of four epitope-forming amino acids, and two associating functional groups. The epitope-forming amino acids may have the same or alternating-stereochemical configurations; i.e., L-L-L-L, D-D-D-D, L-D-L-L, L-L-D-L, L-L-L-D, D-L-L-L, L-L-D-D, D-D-L-L, L-D-L-D, D-L-D-L, L-D-D-L, D-L-L-D, D-L-D-D, D-D-L-D, D-D-D-L or L-D-D-D.

The associating functional groups are positioned in the cyclic oligopeptide so that they form one or more intra-cyclic associations whereby the cyclic oligopeptide is constrained in a single conformation so that the epitope-forming amino acids form an epitope in each domain. The formation of a single conformation in a cyclic oligopeptide may be measured by a number of different methods, which are well known in the art. Standard spectroscopic methods, such as $^1$H NMR spectroscopy, circular dichroism, optical rotatory dispersion, or X-ray crystallography may be used to determine the conformation of the cyclic oligopeptide The epitope-forming amino acids form an epitope in each domain because the cyclic oligopeptide are constrained in a single conformation by the one or more intra-cyclic associations. The epitopes formed are capable of specifically binding to a target ligand. The specific structure of the epitope and target ligand is not limited in the present invention. The purpose of this invention is to provide an oligopeptide scaffold which presents a plurality of epitopes comprised of any appropriate combination of at least two epitope-forming amino acids, analogues or derivatives thereof, in such a way that these epitope-forming amino acids are maintained in a stable configuration possessing sufficient rigidity to enable the epitope to bind strongly to a specific target ligand, such as a receptor. The skilled person may know the sequence of epitope-forming amino acids or may use a method such as that disclosed in WO 01/01140 for providing an epitope which interacts with target ligand. The skilled person does not need detailed chemical structures of all possible epitopes because he can easily select suitable amino acids to form an epitope. Any sequence of epitope-forming amino acids may be suitable in any given situation and this will depend upon the target ligand. Further, the order of the amino acids in each domain may determine the activity of the epitope formed and will also depend upon the target ligand. It is not necessary to know the exact chemical structure of the ligand provided that the biological activity of the target ligand is known. Epitope-forming amino acids may be included in the cyclic oligopeptide of the present invention without the need for knowledge of the exact chemical structure of the ligand because the biological function associated with the ligand can be measured to determine whether or not epitope ligand interaction has occurred. The skilled person, on the basis of experimental data obtained in the appropriate test model, can easily select amino acids to include in the cyclic oligopeptide as the epitope forming amino acids and determine which order of amino acids in each domain provides the best biological activity by testing for the desired activity.

Examples of assays for determining the interaction between the cyclic oligopeptide and the target ligand may include binding assays such as those utilising the ELISA principle for detection of association between antibody and antigen. Other suitable in vitro assays include modification of fluorescence of environmentally-sensitive membrane-bound fluorescent probes, precipitation reactions, enhancement or inhibition of enzyme activity etc. Assays relying on the ability of materials to alter the behaviour of cells cultured in vitro may also be appropriate, such as assays for cell death, cell proliferation, apoptosis, inhibition or stimulation of cell-to-cell contact, secretion of cytokines or other soluble products, synthesis of specific m-RNA, intracellular vesicular transport, alteration of cell signalling processes etc. In vivo assays in whole animals or humans may also be carried out, for example incorporation of radiolabel into the cyclic oligopeptide, followed by investigation of its subsequent distribution after administration by various routes.

An epitope is formed in each domain. Therefore, the number of epitopes formed in the cyclic oligopeptide is at least two, preferably two or three. The epitopes in the cyclic oligopeptide may be the same or different. When the epitopes in the cyclic oligopeptide are different, each domain may have different amino acids or have the same amino acids but in a different order. An example of such an epitope is that formed by the combination of the amino acids serine (S), phenylalanine (F) and arginine (R), which bind to a cell surface receptor on macrophages. Binding of the epitope to the cell surface receptor causes TNT secretion to be inhibited.

Intra-cyclic Associations

The one or more intra-cyclic associations serve to constrain the cyclic oligopeptide in a single conformation with a plurality of amino acid domains. The epitope-forming amino acids in each domain are tightly constrained with very limited freedom of motion. This allows the formation of a stable epitope in each domain which can interact with improved stability and specificity with the target ligand to produce a biological response.

The number of associating functional groups in each cyclic oligopeptide and the type of associating functional groups selected will depend upon the epitope forming amino acids and the target ligand. The number and nature of the associating functional groups may affect the biological activity of the cyclic oligopeptide. The skilled person can easily select the most effective number or type of associating functional groups to use by testing for the desired activity.

The one or more intra-cyclic associations are formed by two or more appropriately positioned associating functional groups. At least one associating functional group is preferably positioned between each of the amino acid domains.

The one or more intra-cyclic associations may be covalent or non-covalent. The associating functional groups in the cyclic oligopeptide may be the same or different.

The associating functional groups may be borne on associating amino acids. In one embodiment the associating functional groups are the side chains of the associating amino acids or the modified side chains of the associating amino acids or the groups added onto the side chain of the associating amino acids. An example of this embodiment is depicted in structure I below.

Alternatively, the associating functional groups may be borne on the nitrogen atoms of peptide linkages in the cyclic oligopeptide ring by substitution of the hydrogen bonded to the nitrogen. An example of this embodiment is depicted in structure II below.

In a further alternative embodiment, the associating functional groups may be borne on other suitable groups positioned within the oligopeptide ring, which are not amino acids. An example of such a group is an alpha hydroxy carboxylic acid, where the hydroxy group participates in an ester-linkage, instead of a peptide linkage.

The wording "two or more associating functional groups" include the following embodiments:

where the intra-cyclic association is non-covalent:
- the associating functional groups are two pendant groups from the oligopeptide ring borne on associating amino acids within the ring, which associate to form the non-covalent association;
- the associating functional groups are two pendant groups from the oligopeptide ring borne on nitrogen atoms of peptide linkages within the ring, which associate to form the non-covalent association;
- the associating functional groups are two pendant groups from the oligopeptide ring borne on other suitable groups positioned in the ring, which associate to form the non-covalent association; or where the intra-cyclic association is covalent:
- the associating functional groups are two groups borne on associating amino acids within the ring, which are bonded together to form the covalent association either directly or via a linker, such as a bi-functional group;
- the associating functional groups are two groups borne on nitrogen atoms of peptide linkages within the ring, which are bonded together to form the covalent association either directly or via a linker, such as a bi-functional group; or
- the associating functional groups are two groups borne on other suitable groups positioned in the ring, which are bonded together to form the covalent association either directly or via a linker, such as a bi-functional group.

The wording "borne on" means that the associating groups are either directly bonded or attached via a suitable linker to the associating amino acids, nitrogen atoms or other suitable groups.

In a preferred embodiment, the one or more intra-cyclic associations between the associating functional groups are non-covalent. Non-covalent intra-cyclic associations are particularly preferred in the present invention because they allow the cyclic oligopeptide to have the right balance between rigidity and flexibility. The cyclic oligopeptide is rigid enough to keep the peptide backbone in one conformation and ensure that the epitope-forming amino acids are positioned close enough together and correctly to form an epitope capable of specifically binding to a target ligand. The cyclic oligopeptide is also flexible enough to allow sufficient movement of the side chains of the epitope-forming amino acids to adapt to the precise structure of the target ligand to which they can bind. Therefore, cyclic oligopeptides of the present invention comprising non-covalent intra-cyclic associations can interact with improved stability and specificity with a target ligand to produce a biological response.

Preferably the intra-cyclic associations are hydrophobic. In a particularly preferred embodiment there are two amino acid domains and two lipophilic associating functional groups.

The use of non-covalent intra-cyclic associations, particularly by hydrophobic interactions, is advantageous because it allows intra-cyclic associations to be formed from interactions between three or more associating functional groups. This permits the formation of three or more amino acid domains, which is difficult when covalent intra-cyclic associations are used. Accordingly, in other preferred embodiments of the present invention the cyclic oligopeptide may comprise three or more associating functional groups which form intra-cyclic associations to produce three or more amino acid domains. The use of lipophilic associating functional groups to form non-covalent intra-cyclic associations by hydrophobic interactions is particularly advantageous when the cyclic oligopeptide is large.

The associating functional groups, which position to form the non-covalent one or more intra-cyclic associations, may comprise any molecule which is borne on a suitable group of appropriate stereochemistry which forms part of the cyclic oligopeptide ring. The associating functional groups are preferably borne on associating amino acids or analogues thereof, examples of which are cited below, although other groups capable of insertion in the cyclic oligopeptide ring may be employed. It is generally preferred that the groups on which the associating functional groups are borne are linked in the ring by peptide bonds. In an alternative embodiment, one or more of the peptide bonds may be replaced by other types of linkage. Examples of such linkages are ester linkages, ether linkages, thio ester linkages and thio ether linkages. This may be desirable on occasion in order to limit attack by proteases in biological fluids.

The associating amino acids may comprise natural amino acids bearing the associating fractional groups.

Preferably, the associating amino acids are lipidic amino acid analogues. For example, the associating amino acids may comprise from cysteine, glycine, lysine, aspartic acid or glutamic acid. In the case of cysteine, the associating functional group may be an aliphatic group added onto the side chain of the cysteine via the sulphydryl functionality. Lysine, aspartic acid and glutamic acid may also be employed in this way, by adding the associating functional group onto the side chain. The associating amino acid may alternatively be an amino acid in which the side chain residue is a single aliphatic group, which constitutes the associating functional group. For example, if an associating amino acid is based on glycine, the alpha hydrogen of the glycine may be replaced by an aliphatic group, which constitutes the associating functional group.

The aliphatic group referred to above, which may form the associating functional group, is preferably an aliphatic hydrocarbon chain preferably having from 8 to 20 carbon atoms and more preferably comprises from 10 to 16 carbon atoms, most preferably 10 or 12 carbons and may be saturated or unsaturated, straight-chain or branched chain and unsubstituted or substituted either wholly or partially, for example with halogen atoms. Alternatively, the aliphatic group may be composed of silane moieties.

In the example structure I below, the associating amino acid is glycine, in which the alpha hydrogen has been replaced by a $C_{10}$ hydrocarbon chain.

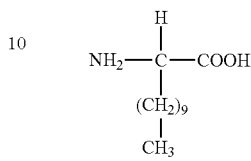

In one embodiment, where the associating functional groups are borne on the nitrogen atoms of peptide linkages in the ring, non-covalent intra-cyclic associations, such as hydrophobic associations, may be brought about by substituting the hydrogen atoms on the nitrogens of the peptide linkages by the associating functional groups such as, for example, the aliphatic group, as defined above.

Substitution of a hydrogen atom on a nitrogen of a peptide linkage in the cyclic oligopeptide of the present invention by an associating functional group may be made by first substituting the hydrogen atom with a methylene groups bearing a suitable functional group such as, for example, —SH, —OH or —NH$_2$, subsequently followed by derivatisation with the associating functional group, such as an aliphatic group as defined above.

In one aspect of this embodiment, where the nitrogen is from a peptide bond linking two epitope-forming amino acids from separate amino acid domains, the cyclic oligopeptide of the present invention may have the following structure II:

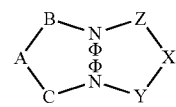

wherein A, B, C, X, Y and Z represent the epitope-forming amino acids, N represents the nitrogen of peptide linkages between B/Z and C/Y and Φ represents the associating functional groups, such as an aliphatic group as defined above, attached to nitrogen.

A further advantage of using non-covalent, particularly hydrophobic, associating functional groups is that this may allow inter-molecular interactions, where the hydrophobic associating functional groups from different cyclic oligopeptides associate with each other to produce dimers or oligomers containing a multiplicity of repeated epitopes oriented in different directions. The extent to which such interactions take place depends on the sequence structure of the cyclic oligopeptide, which determines the relative hydrophilicity of the amino acid domains. This may further be controlled by judicious choice of the associating functional group, where the chirality and bulkiness may be varied to control the precise amount of hydrophobic surface of the oligopeptide exposed. This may be advantageous in modulating intermolecular interactions with other internally-constrained cyclic oligopeptides, or interactions with other molecules such as proteins or cyclodextrins. This may be advantageous in creating small multimeric structures comprising two or more cyclic oligopeptides of the present invention, which can bind to two or more cell-surface receptors at the same time, thereby cross-linking the receptors in such a way that a strong initiation trigger is presented to the cell, resulting in a signal cascade.

Interactions of cyclic oligopeptides of the present invention with other non-identical cyclic oligopeptides of the present invention may be advantageous in creating multimeric structures which possess multiple functionality by virtue of the different epitopes contributed to the structure by the different oligopeptides. Thus, for example, one oligopeptide may comprise one or more epitopes which bind to receptors which allow the multimeric structure to be internalised, while a second oligopeptide within the multimeric structure may comprise one or more epitopes which can interact with components of a signalling cascade inside the cell, after internalisation.

Binding of cyclodextrins to the cyclic oligopeptides of this invention may help reduce the level of interactions between the hydrophobic parts of different oligopeptides, and thus prevent the formation of large aggregates, whose activity may be reduced compared with monomers or oligomers because of steric hindrance of epitopes in these large aggregates.

In solutions of proteins such as albumin or gelatin, one or more of the cyclic oligopeptides of the invention may bind to the surface of the protein as a result of association of the lipophilic moieties of the hydrophobic associating functional groups in the peptide with regions of the protein which possess an affinity for alkyl or acyl hydrocarbon chains. Such binding of one or more cyclic oligopeptides of the present invention on the surface of a large protein is one way of arranging that a multiple array of epitopes on the cyclic oligopeptides is presented in such a way that triggering signalling interactions in cells is maximised.

In a further embodiment, the one or more intra-cyclic associations between the associating functional groups are covalent. In this embodiment, the associating functional groups may also be borne on associating amino acids. For example, the associating functional groups may be the side chains of cysteines (associating amino acids) and the association is formed by an intra-cyclic di-sulphide bond between these side chains. Alternatively, the associating amino acids may be lysine and glutamic acid, which can associate covalently by formation of a peptide linkage through the terminal groups on their side chains (associating functional groups), or glutamic acid and serine, which can react to form an ester linkage. Analogues of these amino acids bearing the same functional moieties can also be used.

In one embodiment, a covalent intracyclic association may be achieved by substituting hydrogens attached to the nitrogen atoms of peptide linkages in the ring with the associating functional groups, which form covalent associations. The associating functional groups may be thiols, or other chains bearing functional groups at their termini which can form a covalent association. Substitution of a hydrogen atom on a nitrogen of a peptide linkage in the cyclic oligopeptide of the present invention by an associating functional group may be made by first substituting the hydrogen atom with a methylene group bearing a suitable functional group such as, for example, —SH, —OH or —$NH_2$, subsequently followed by a second step of linking the functional group to a bi-functional reagent. The covalent association is formed by additionally substituting a second hydrogen atom (on a nitrogen of a peptide linkage situated at a suitable position within the cyclic oligopeptide) with a second methylene group bearing a suitable functional group and the above bi-functional reagent is additionally linked to the functional group of this second methylene group to create a covalent linkage between two nitrogen atoms of peptide linkages in the cyclic oligopeptide.

Depending on the nature of the associating functional groups incorporated into the cyclic oligopeptides, appropriate bifunctional reagents would be those which comprise a short chain in which each of the termini possesses a functional group selected from, but not limited to the following list: carboxyl, amino, hydroxyl, sulphydryl, bromo, iodo, cyano, azo and boronic acids groups.

In a particular aspect of the present invention wherein the cyclic oligopeptide comprises two amino acid domains and two associating functional groups, each borne on an associating amino acid, and an epitope is formed from three epitope-forming amino acids in each domain, the cyclic oligopeptide may have the following structure:

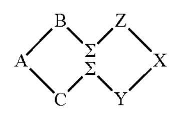

wherein A, B, C, X, Y and Z represent the epitope-forming amino acids; A and X represent D amino acids and B, C, Y and Z represent L amino acids or A and X represent L amino acids and B, C, Y and Z represent D amino acids; one epitope is formed from the domain C-A-B and one epitope is formed from the domain Z-X-Y; and each Σ represents an associating amino acid bearing an associating functional group.

In one example of a cyclic oligopeptide according to the present invention, the Z-X-Y and/or the C-A-B domain may be selected from the amino acid sequences RFS, RSF, FSR, FRS, SRF, SFR, QLS, QSL, SQL, SLQ, LQS or LSQ and each Σ is a lipidic amino acid with a $C_{10}$ linear hydrocarbon side chain as the associating functional group. Preferably the Z-X-Y domain is RFS in which it is preferred that phenylalanine is of D configuration, serine is of L configuration, arginine is of L configuration and each lipidic amino acid is of L configuration. In a preferred embodiment the Z-X-Y domain and/or the C-A-B domain selected from the sequences above each form an epitope capable of suppressing TNF secretion. Accordingly, these sequences may be useful in the treatment of a disease wherein TNF is an exacerbating factor for example, a disease is selected from cancer, obesity, cardiac disorders, autoimmune disease and inflammatory diseases. Theses sequences may be used to treat an autoimmune disease selected from rheumatoid arthritis, Multiple Sclerosis and Crohn's disease.

In the above structure, the domain C-A-B may be the same as or different from the domain Z-X-Y.

In a further aspect of the present invention the cyclic oligopeptide comprises three amino acid domains and an epitope is formed from the three epitope-forming amino acids in each domain and preferably the oligopeptide comprises three associating functional groups.

In a further aspect of the present invention the cyclic oligopeptide comprises two domains and an epitope is formed from four epitope-forming amino acids in each domain. In one embodiment of this aspect of the invention the cyclic oligopeptide has the following structure:

wherein A, B, C, D, W, X, Y and Z represent the epitope-forming amino acids; one epitope is formed from the domain D-C-A-B and one epitope is formed from the domain Z-X-Y-W; and each Σ represents an associating amino acid.

In an alternative embodiment of this aspect of the invention the cyclic oligopeptide has the following structure:

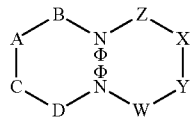

wherein A, B, C, D, W, X, Y and Z represent the epitope-forming amino acids; one epitope is formed from the domain D-C-A-B and one epitope is formed from the domain Z-X-Y-W; each N represents the nitrogen of peptide linkages between B-Z and C-Y and each Φ represents an associating functional group attached via the nitrogen.

In one example of a cyclic oligopeptide according to this aspect of the present invention, the Z-X-Y-W domain and/or the D-C-A-B domain may be selected from the amino acid sequences YEKA (SEQ ID NO: 1), YEAK (SEQ ID NO: 2), YAKE (SEQ ID NO: 3), YAEK (SEQ ID NO: 4), YKAE (SEQ ID NO: 5), YKEA (SEQ ID NO: 6), EYKA (SEQ ID NO: 7), EYAK (SEQ ID NO: 8), EKAY (SEQ ID NO: 9), EKYA (SEQ ID NO: 10), EAKY (SEQ ID NO: 11), EAYK (SEQ ID NO: 12), KAYE (SEQ ID NO: 13), KAEY (SEQ ID NO: 14), KYAE (SEQ ID NO: 15), KYEA (SEQ ID NO: 16), KEAY (SEQ ID NO: 17), KEYA (SEQ ID NO: 18), AKEY (SEQ ID NO: 19), AKYE (SEQ ID NO: 20), AYEK (SEQ ID NO: 21), AYKE (SEQ ID NO: 22), AEYK (SEQ ID NO: 23) or AEKY (SEQ ID NO: 24) and each ρ is a lipidic amino acid with a linear hydrocarbon side chain associating functional group comprising a hydrocarbon chain between 8 and 20 carbons in length. Preferably the Z-X-Y-W domain is YEKA (SEQ ID NO: 1) and the D-C-A-B domain is EYAK (SEQ ID NO: 8). In a preferred embodiment the Z-X-Y-W domain and/or the D-C-A-B domain selected from the sequences above each form an epitope capable of inhibiting proteolytic activity. Accordingly, these sequences may be used for treating a disease wherein protease activity is an exacerbating factor such as cardiovascular disease, circulation disorders and HIV.

In one embodiment of this aspect of the invention, the domain D-C-A-B is the same as the domain Z-X-Y-W.

Compositions

In a further aspect, the present invention provides a pharmaceutical composition comprising the cyclic oligopeptide as defined above and a pharmaceutically acceptable excipient and/or adjuvant. The excipient is preferably selected from transcutol, poloxamer block-copolymers, cyclodextrins, non-ionic surfactants or bile salts. If the excipient is a non-ionic surfactant it is preferably selected from acyl esters of polyethylene glycol or aliphatic ethers of polyethylene glycol.

As discussed above, in one embodiment of the invention inter-cyclic associations may form between separate cyclic oligopeptides where hydrophobic associating functional groups from different cyclic oligopeptides associate with each other to produce dimers or oligomers containing a multiplicity of repeated epitopes oriented in different directions. The extent of inter-cyclic interactions can be modified by co-mixing with excipients which assist in solubilisation of hydrophobic moieties in aqueous media.

Uses

In a further aspect, the present invention provides a cyclic oligopeptide as defined above or a composition as defined above, for use as a medicament, a prophylactic or a diagnostic.

The present invention also provide the use of a cyclic oligopeptide as defined above or a composition as defined above for the manufacture of a medicament for treating a disease wherein TNF is an exacerbating factor. Preferably the disease is selected from obesity, cardiac disorders, autoimmune disease and inflammatory diseases. More preferably the disease is rheumatoid arthritis or Crohn's disease. The cyclic oligopeptide as defined above may be used to treat cancer wherein TNF is an exacerbating factor. The cancer may be benign or malignant. The cancer is preferably a solid tumor. Such cancers include but are not limited to ovarian cancer, breast cancer, skin cancers and epithelial cancers.

The present invention also provides use of a cyclic oligopeptide as define above or a composition as defined above for the manufacture of a medicament for treating a disease wherein protease activity is an exacerbating factor, including cardiovascular disease, circulation disorders and HIV. In one specific embodiment of the invention, each domain in the cyclic oligopeptide comprises epitope-forming amino acids SRER (SEQ ID NO: 25), SERE (SEQ ID NO: 26), EYKA (SEQ ID NO: 7), YEAK (SEQ ID NO: 2), SFR or RFS, which were shown in example 7 to inhibit thrombin proteolytic activity.

In one specific embodiment of this invention described above, the cyclic oligopeptide comprises the amino acids serine, phenylalanine and arginine as the epitope-forming amino acids in at least one of the domains. These oligopeptides have been shown to display activity in inhibition of secretion of TNF from macrophages. In a preferred aspect of this embodiment the associating functional groups are lipidic amino acids with $C_{12}$ hydrocarbon side chains and the epitope-forming amino acids are selected from RFS, FSR or SRF, where the central amino acid is in the D form, and the outer two amino acids are in the L form. Each epitope in the cyclic oligopeptide may be the same or different.

By virtue of their ability to down-regulate TNF secretion, these oligopeptides may have efficacy in treatment of such diseases as rheumatoid arthritis, Crohns disease, Multiple Sclerosis obesity, cardiac disorders, autoimmune disease, and other ailments where inflammatory process are involved. By virtue of their ability to down-regulate TNF secretion, these oligopeptides may also have efficacy in treatment of cancer wherein TNF is an exacerbating factor. The cancer may be benign or malignant. The cancer is preferably a solid tumor. Such cancers include but are not limited to ovarian cancer, breast cancer, skin cancers and epithelial cancers.

In one specific embodiment of this invention described above, the cyclic oligopeptide comprises the amino acids A, K, E and Y as the epitope-forming amino acids in at least one of the domains. These oligopeptides have been shown to display activity in inhibition of secretion of TNF from macrophages. In a preferred aspect of this embodiment the associating functional groups are lipidic amino acids with $C_{10}$ hydrocarbon side chains and the epitope-forming amino acids are selected from YEKA (SEQ ID NO: 1) and EYAK (SEQ ID NO: 8). Each epitope in the cyclic oligopeptide may be the same or different. The efficacy of Copaxone (Glatiramer acetate), a random copolymer comprising amino acids A, K, E and Y, in treatment of multiple sclerosis, is considered to be reflected by the ability of this compound to down-regulate TNF secretion in vitro. (Ref: Weber MS, Starck M, Wagenpfeil S, Meinl E, Hohlfeld R & Farina C. *Multiple sclerosis:*

*glatiramer acetate inhibits monocyte reactivity in vitro and in vivo*. Brain 127 pp1370-8 (2004)). In this regard, the cyclic oligopeptide cyclo(-A-K-Σ-Y-E-K-A-Σ-E-Y) tested in example 6 will also be useful in treatment of multiple sclerosis, since it comprises the same amino acids in a non-random configuration and displays the same effect on TNF secretion by macrophages. Other sequences arrangments of A, K, E and Y in cyclic oligopeptides according to the present invention may also be used to treat Multiple Sclerosis.

An advantage of the invention is that strong specific binding interactions can be achieved with the cyclic oligopeptide of the present invention in comparison to conventional biological receptors. The cyclic oligopeptide may be relatively small, preferably comprising no more than 6 or 8 amino acids. Accordingly, the cyclic oligopeptide according to the present invention can be made far less immunogenic than their protein counterparts.

In accordance with this aspect of the invention, not only can the cyclic oligopeptide of the present invention be formulated to interact with a ligand in vitro but also the composition can be used in vivo.

The cyclic oligopeptide or composition according to the present invention may be administered via any route appropriate to the disease in question, including, but not limited to, oral, nasal, rectal, buccal, sub lingual, pulmonary, vaginal, topical, ocular, otic, sub-cutaneous, intra-dermal, intra-articular, intra-thecal, intra-muscular, intra-cerebral, intra-cranial and intravenous routes of administration.

The cyclic oligopeptides may be administered in free aqueous solution, or in conjunction with pharmaceutical excipients in the composition of the present invention. The cyclic oligopeptide or composition may also be co-mixed with other active molecular principles to synergise with, or otherwise enhance their activity as medicinal therapeutic agents. When administered by certain routes, eg oral or rectal, the oligopeptides or composition may be formulated as solids, semi-solids or liquids and filled into capsules, or as solids compressed into tablets, or extruded in pellets. In this case, the capsules, tablets or pellets may be enteric coated, if the final route of administration is to be oral. For topical application, formulation as a gel, a paste or an oil is particularly suitable, while for pulmonary or nasal administration the oligopeptide may be in the form of an aerosol.

Method

In a further aspect, the present invention provides a method for producing a cyclic oligopeptide as defined above, comprising:
  i) selecting the epitope-forming amino acids;
  ii) producing a cyclic oligopeptide incorporating the epitope-forming amino acids.

Methods are known for identifying epitopes. In traditional combinatorial chemistry, the identification of the most favourable sequence for binding to a specific receptor must be carried out by synthesis of hundreds of possible combinations of different groups such as amino acids, in different orders, each one having to be tested for efficacy. This process is time-consuming, expensive and is limited by the nature of the chemistry which can be carried out in linking the different components together.

As discussed above, the epitope-forming amino acids may be selected by a variety of different methods known to the person skilled in the art.

WO 01/01140 provides a method for determining molecules which form an epitope capable of interacting with a desired ligand which uses a non-covalent assembly of a plurality of distinct conjugates. As described on pages 2 to 5 of WO 01/01140, each conjugate comprises a head group and a tail group, wherein the tail groups of the conjugates form a hydrophobic aggregation and the conjugates have freedom of motion with respect to each other within the assembly so that, in the presence of a ligand, at least two of the head groups (which are the same or different) are appropriately positioned to form an epitope capable of interacting with the ligand more strongly than each of head groups individually. The head groups are typically hydrophilic and the tail groups typically hydrophobic, eg lipophilic, composed of hydrocarbon chains, halophilic, constructed of fluorocarbon chains, or silane based. By constructing conjugates with a head group and a tail group, the tail groups can associate to form a hydrophobic aggregation which is typically a supramolecular assembly such as a micelle, a lamellar structure, a liposome or other lipid structure, in which the conjugate are oriented whereby the head groups are brought into close proximity when in an aqueous phase. Because the conjugates are movable within the assembly, the head groups are able to adopt a number of different positions within the assembly. The head groups, which are typically non-identical, are therefore free to move within the assembly and, surprisingly, to interact cooperatively to induce biological consequences which the head groups on their own are not capable of eliciting.

In a preferred embodiment of the present invention, the method disclosed in WO 01/01140 is used to select the epitope-forming amino acids, wherein this method comprises:
  (a) selecting a set of conjugates, each conjugate comprising a head group and a tail group, with an array of head groups, wherein each head group comprises an amino acid;
  (b) forming a non-covalent association therefrom, in which the tail groups aggregate hydrophobically and in which the conjugates are movable;
  (c) assaying for sufficient interaction between the noncovalent association and the target ligand;
  (d) optionally repeating steps (a) to (c) using a set of conjugates with a modified array of head groups; and
  (e) on finding sufficient interaction in step (c) selecting the amino acids of the head groups of the set of conjugates as the epitope-forming amino acids in step (a).

Examples of assays for "sufficient interaction" may include binding assays such as those utilising the ELISA principle for detection of association between antibody and antigen. Other suitable in vitro assays include modification of fluorescence of environmentally-sensitive membrane-bound fluorescent probes, precipitation reactions, enhancement or inhibition of enzyme activity etc. Assays relying on the ability of materials to alter the behaviour of cells cultured in vitro may also be appropriate, such as assays for cell death, cell proliferation, apoptosis, inhibition or stimulation of cell-to-cell contact, secretion of cytokines or other soluble products, synthesis of specific m-RNA, intracellular vesicular transport, alteration of cell signalling processes etc. In vivo assays in whole animals or humans may also be carried out, for example incorporation of radiolabel into the supramolecular assemblies, followed by investigation of its subsequent distribution after administration by various routes.

According to this method a combinatorial approach is used in which a range of different supra-molecular assemblies (or "probes") is prepared, each containing a different combination of conjugates selected from a pre-synthesised bank. Selection of the appropriate conjugates may be based on known properties of the target ligand or may simply involve the use of a very wide range of head groups to increase the probability that two or more of the head groups will form an epitope for the ligand. In this way, following the assay for sufficient interaction between the probe and the ligand as described above, the combination of conjugates found to be most effective may be modified by adding further head groups, removing some head groups, or both, and assaying the resultant probes once again for sufficient interaction. Eventually, the most favourable combination of head groups may be identified and selected for use as the epitope-forming amino acids.

EXAMPLES

Example 1

Dose Response of Cyclic Oligopeptide in Suppressing TNF Secretion Stimulated by Lipopolysaccharide (LPS) in a Macrophage Cell Line 1. A cyclic octapeptide with the structure:

cyclo(-DF-S-Σ-R-DF-S-Σ-R-)

was synthesised using standard methods based on the Merrifield resin-based technique, followed by solution-phase cyclisation. The purified peptide was prepared as a solution in distilled water at a concentration of 1 mg/ml.
   R, F and S represent the epitope-forming amino acids and Σ represents the associating functional group borne on the associating amino acid wherein the associating amino acid is an L-alpha aminocarboxylic acid and the associating functional group is a side-chain residue consisting of a straight aliphatic chain containing ten carbon atoms.
   All amino acids are in the L form unless indicated otherwise.
   All amino acids are linked by peptide bonds.
2. J774A.1 cells (a macrophage cell line) were plated out in all the wells of a 24-well cluster plates at a seeding density of $5 \times 10^5$ cells/ml/well (1 ml RPMI 1640 culture medium per well), and incubated overnight at 37° C. in 5% $CO_2$/air.
3. The following day, the solution from step 1 was administered to fifteen wells containing cells in step 2, to give three wells each with a final concentration of 50, 25, 12.5, 6.25 or 3.125 ug/ml. The remaining wells were left untreated. The plate was incubated for a further four hours at 37 degC.
4. Lipopolysaccharide (from *E. coli* strain 0111 B4) was added to the wells receiving the octapeptide solution, as well as three of the wells receiving no peptide. The final concentration of lipopolysaccharide was 0.625 ug/ml.
5. The plate was incubated overnight, and the following day the supernatants were assayed for TNF using a commercial ELISA kit.

Results obtained, shown in the table below, demonstrate that the activity of the cyclic oligopeptide in suppressing TNF secretion stimulated by LPS is dose related.

| Concentration of Peptide (ug/ml) | TNF concentration (pg/ml) | Standard deviation |
|---|---|---|
| 0 | 1780.09 | 136.49 |
| 3.125 | 1494.53 | 127.83 |
| 6.25 | 1346.20 | 45.84 |
| 12.5 | 1037.31 | 90.01 |
| 25.0 | 621.75 | 14.53 |
| 50.0 | 613.70 | 15.46 |

Example 2

The Effect of Cyclic Oligopeptides with Varying Associating Functional Groups in Suppressing TNF Secretion Stimulated by Cholera Toxin B (CTB) Fragment in a Macrophage Cell Line 1. Cyclic oligopeptides were prepared with the following structures:

cyclo(-DF-R-$\Sigma_{10}$-S-DF-R-$\Sigma_{10}$-S-)

cyclo(-DF-S-$\Sigma_{10}$-R-DF-S-$\Sigma_{10}$-R-)

cyclo(-DF-R-$\Sigma_4$-S-DF-R-$\Sigma_4$-S-)

cyclo(-DF-S-$\Sigma_4$-R-DF-S-$\Sigma_4$-R-)

wherein S, F and R represent the epitope-forming amino acids, Σ represents the associating functional group borne on the associating amino acid, wherein $\Sigma_{10}$ represents a racemic associating amino acid which is an aminocarboxylic acid and the associating functional group is a side-chain residue consisting of an unbranched —$C_{10}H_{21}$ and $\Sigma_4$ indicates norleucine, wherein the associating functional group is the side chain of four carbons.

These cyclic oligopeptides were prepared as solutions in transcutol at a concentration of 5 mg/ml, then diluted to a concentration of 1 mg/ml by addition of distilled water.
2. J774A.1 cells (a macrophage cell line) were plated out in all the wells of a 24-well cluster plates at a seeding density of $3 \times 10^5$ cells/ml/well (1 ml RPMI 1640 culture medium per well), and incubated overnight at 37° C. in 5% $CO_2$/air.
3. The following day, the solutions from step 1 were administered to twelve wells containing cells in step 2, to give three wells each with a final concentration of 12.5 ug/ml. The remaining wells were left untreated. The plate was incubated for a further four hours at 37 degC.
4. Cholera toxin B (CTB) fragment was added to the wells receiving the octapeptide solutions, as well as three of the wells receiving no peptide. The concentration of cholera toxin B fragment was 10 ug/ml.
5. The plate was incubated overnight, and the following day the supernatants were assayed for TNF using a commercial ELISA kit.

Results obtained, shown in the table below, demonstrate that the presence of long-chain hydrocarbon side-chains consisting of an unbranched —$C_{10}H_{21}$ as the associating functional group gives rise to activity of the cyclic oligopeptides in suppressing TNF secretion stimulated by cholera toxin B fragment. Cyclic oligopeptides where the associating functional group has a chain length of only four carbons do not possess any inhibitory activity.

| Peptide | Concentration of TNF (pg/ml) | Standard deviation |
|---|---|---|
| Medium control | 67.5 | 6.7 |
| cyclo(-DF-R-$\Sigma_{10}$-S-DF-R-$\Sigma_{10}$-S-) + CTB | 268.5 | 17.9 |
| cyclo(-DF-S-$\Sigma_{10}$-R-DF-S-$\Sigma_{10}$-R-) + CTB | 85.7 | 13.6 |
| cyclo(-DF-R-$\Sigma_4$-S-DF-R-$\Sigma_4$-S-) + CTB | 664.4 | 57.1 |
| cyclo(-DF-S-$\Sigma_4$-R-DF-S-$\Sigma_4$-R-) + CTB | 621.1 | 25.3 |
| CTB alone | 690.8 | 58.6 |

Example 3

The Effect of Cyclic Oligopeptides with Varying Epitope-forming Amino Acids and Stereochemical Configurations of the Associating Amino Acids in Suppressing TNF Secretion Stimulated by Lipopolysaccharide (LPS) in a Macrophage Cell Line 1. Cyclic octapeptides were prepared with the following structures:

cyclo(-DF-S-$\Sigma_L$-R-DF-S-$\Sigma_L$-R-)

cyclo(-DF-S-$\Sigma_L$-R-DF-S-$\Sigma_D$-R-)

cyclo(-DF-S-$\Sigma_D$-R-DF-S-$\Sigma_D$-R-)

cyclo(-DF-R-$\Sigma_L$-S-DF-R-$\Sigma_L$-S-)

cyclo(-DF-R-$\Sigma_L$-S-DF-R-$\Sigma_D$-S-)

cyclo(-DF-R-$\Sigma_D$-S-DF-R-$\Sigma_D$-S-)

wherein F, S and R are the epitope-forming amino acids, $\Sigma_L$ represents an associating amino acid which is an L-alpha aminocarboxylic acid in which the associating functional group is a side-chain residue consisting of an unbranched —$C_{10}H_{21}$; $\Sigma_D$ represents an associating amino acid which is a D-alpha aminocarboxylic acid in which the associating functional group is a side-chain residue consisting an unbranched —$C_{10}H_{21}$. These cyclic oligopeptides were prepared as solutions in distilled water at a concentration of 1 mg/ml.
2. J774-1 cells (a macrophage cell line) were plated out in all the wells of a 24-well cluster plates at a seeding density of $3\times10^5$ cells/ml/well (1 ml RPMI 1640 culture medium per well), and incubated overnight at 37° C. in 5% $CO_2$/air.
3. The following day, the solutions from step 1 were administered to eighteen wells containing cells in step 2, to give three wells each with a final concentration of 50 ug/ml. The remaining wells were left untreated. The plate was incubated for a further four hours at 37 degC.
4. Lipopolysaccharide (from *E. coli* strain 0111 B4) was added to the wells receiving the octapeptide solutions, as well as three of the wells receiving no peptide. The concentration of lipopolysaccharide was 1.25 ug/ml.
5. The plate was incubated overnight, and the following day the supernatants were assayed for TNF using a commercial ELISA kit.

Results obtained, shown in the table below, demonstrate that cyclic oligopeptides containing amino acids in the order R-DF-S have high activity in suppressing TNF secretion stimulated by LPS, and that the presence of at least one associating amino acid which is L-alpha aminocarboxylic acid with an associating functional group which is a side-chain residue consisting of an unbranched —$C_{10}H_{21}$ is required, the other associating amino acid being the same aminocarboxylic acid in either the L or D form.

| Peptide | Concentration of TNF (pg/ml) | Standard deviation |
| --- | --- | --- |
| LPS alone | 1861.9 | 108.7 |
| cyclo(-DF-S-$\Sigma_L$-R-DF-S-$\Sigma_L$-R-) + LPS | 865.4 | 68.1 |
| cyclo(-DF-S-$\Sigma_L$-R-DF-S-$\Sigma_D$-R-) + LPS | 987.1 | 16.1 |
| cyclo(-DF-S-$\Sigma_D$-R-DF-S-$\Sigma_D$-R-) + LPS | 1438.0 | 32.6 |
| cyclo(-DF-R-$\Sigma_L$-S-DF-R-$\Sigma_L$-S-) + LPS | 1990.4 | n/a |
| cyclo(-DF-R-$\Sigma_L$-S-DF-R-$\Sigma_D$-S-) + LPS | 1625.2 | 59.6 |
| cyclo(-DF-R-$\Sigma_D$-S-DF-R-$\Sigma_D$-S-) + LPS | 1573.3 | 45.0 |

Binding of cyclodextrins to the cyclic oligopeptides of this invention helps to reduce the level of interactions between the hydrophobic parts of different oligopeptides, and thus prevent the formation of large aggregates, whose activity may be reduced compared with monomers or oligomers because of steric hindrance of epitopes in these large aggregates.

Example 4

Dose Related Effect of an Internally Constrained Cyclic Oligo Peptide Formulated with Hydroxypropyl Beta-cyclodextrin, and Containing Epitopes Formed from the Epitope-forming Amino Acids R-dF-S, in Suppressing TNF Secretion Stimulated by Lipopolysaccharide (LPS) in a Macrophage Cell Line Over a Wide Range of Cyclodextrin Concentrations 1. A cyclic octapeptide with the structure cyclo(-dF-S-$\Sigma$-R-dF-S-$\Sigma$-R-) was prepared as a solution in transcutol at a concentration of 5 mg/ml, where $\Sigma$ represents the associating amino acid as an L-alpha aminocarboxylic acid and the associating functional group borne on the associating amino acid as a side-chain residue consisting of a straight aliphatic chain containing ten carbon atoms.
2. Six separate aliquots of 200 ul of the solution in step 1 were transferred to fresh 8 ml vials and mixed with slow vortexing with 800 ul of a solution of hydroxy-propyl beta cyclodextrin at a concentration 50, 25, 12.5, 6.25, 3.125 or 1.5625 mg/ml in distilled water
2. J774A.1 cells (a macrophage cell line) were plated out in all the wells of a 24-well cluster plates at a seeding density of $5\times10^5$ cells/ml/well (1 ml RPMI 1640 culture medium per well), and incubated overnight at 37° C. in 5% $CO_2$/air.
3. The following day, each of the solutions from step 1 were administered in appropriate volumes to wells containing cells in step 2, to give three wells each with a final concentration of 8, 4, or 2 ug/ml. The remaining wells were left untreated. The plate was incubated for a further four hours at 37 degC.
4. Lipopolysaccharide (from *E. coli* strain 0111 B4) was added to the wells receiving the octapeptide solution, as well as three of the wells receiving no peptide. The final concentration of lipopolysaccharide was 0.625 ug/ml.
5. The plate was incubated overnight, and the following day the supernatants were assayed for TNF using a commercial ELISA kit.

Results obtained, shown in the table below, demonstrate that the activity of the octapeptide in suppressing TNF secretion stimulated by LPS was dose related.

| Concentration of Peptide (ug/ml) | Ratio of Cyclodextrin to peptide by weight | TNF concentration (pg/ml) | Standard deviation |
| --- | --- | --- | --- |
| 0 | — | 2519.3 | 64.4 |
| 2 | 40 | 2450.2 | 61.2 |
| 2 | 20 | 2223.9 | 37.4 |
| 2 | 10 | 2278.3 | 89.4 |
| 2 | 5 | 2177.2 | 110.9 |

-continued

| Concentration of Peptide (ug/ml) | Ratio of Cyclodextrin to peptide by weight | TNF concentration (pg/ml) | Standard deviation |
|---|---|---|---|
| 2 | 2.5 | 2314.2 | 101.8 |
| 2 | 1.25 | 2161.8 | 94.7 |
| 4 | 40 | 1646.5 | 98.4 |
| 4 | 20 | 1488.1 | 16.6 |
| 4 | 10 | 1474.8 | 80.6 |
| 4 | 5 | 1477.5 | 33.2 |
| 4 | 2.5 | 1538.7 | 80.4 |
| 4 | 1.25 | 1599.9 | 106.4 |
| 8 | 40 | 1276.9 | 106.5 |
| 8 | 20 | 1298.4 | 17.3 |
| 8 | 10 | 1218.7 | 20.6 |
| 8 | 5 | 1140.6 | 34.5 |
| 8 | 2.5 | 1105.7 | 35.9 |
| 8 | 1.25 | 1130.9 | 71.8 |

The results demonstrate that formulation of the octapeptide with cyclodextrin gives a significant inhibition of TNF secretion down to a concentration of 2 ug/ml in the tissue culture well, and that this inhibition is achieved over a wide range of cyclodextrin concentrations ranging from 40:1 wt:wt downwards.

Example 5

Effect of an Internally Constrained Cyclic Oligo Peptide Formulated with Hydroxypropyl Beta-Cyclodextrin, and Containing Epitopes Formed from the Epitope-forming Amino Acids R-D-F-S, in Suppressing TNF Secretion Stimulated by Lipopolysaccharide (LPS) in Rats 1. A cyclic octapeptide with the structure cyclo(-DF-S-Σ-R-DF-S-ΣR-), where Σ represents the associating amino acid as an L-alpha aminocarboxylic acid and the associating functional group borne on the associating amino acid as a side-chain residue consisting of a straight aliphatic chain containing ten carbon atoms, was prepared as a solution in transcutol and hydroxypropyl beta-cyclodextrin as described in example 4, where the concentration of peptide was 1 mg/ml, and the final concentration of cyclodextrin was 40 mg/ml.
2. Rats weighing 250 g were injected i.p. with 1 ml of peptide solution (1 mg peptide per rat). A second group of rats received 1 ml of the transcutol/cyclodextrin vehicle containing no peptide. One hour later, the rats were further injected with 1 mg of lipopolysaccharide (from *Salmonella abortus equi*).
3. 150 minutes later, blood samples were taken, and TNF levels measured in the two groups by ELISA. The results shown in the table below demonstrate that the peptide is capable of inhibiting TNF production by cells in response to a stimulus, giving a reduction of greater than 75%.

| | Vehicle | Peptide |
|---|---|---|
| TNF (pg/ml) | 10717 | 2370 |
| SD | 6635 | 1831 |
| No of animals per group | 3 | 5 |

Example 6

Suppression of TNF Secretion by a Cyclic Analogue of Copaxone (Glatiramer Acetate)

1. Two cyclic oligopeptides were prepared with the following structures:

cyclo(-A-K-Σ-Y-E-K-A-Σ-E-Y-)

cyclo(-A-K-Σ-E-Y-K-A-Σ-Y-E-)

All amino acids are in the L form unless indicated otherwise.
    All amino acids are linked by peptide bonds.
    A, K, Y and E represent the epitope-forming amino acids and Σ represents the associating functional group borne on the associating amino acid wherein the associating amino acid is an L-alpha aminocarboxylic acid and the associating functional group is a side-chain residue consisting of a straight aliphatic chain containing ten carbon atoms.
    The cyclic oligopeptides were prepared as solutions in hexafluoro-isopropanol (HFIP) at a concentration of 10 mg/ml, then mixed with equal volumes of HFIP solution containing beta-hydroxypropyl cyclodextrin at a concentration of 50 mg/ml. The organic solutions were then dried down under nitrogen, and the peptide/cyclodextrin complex redissolved in distilled water to give a final concentration of cyclic oligopeptide of 1 mg/ml.
2. J774A.1 cells (a macrophage cell line) were plated out in all the wells of a 24-well cluster plate at a seeding density of $3 \times 10^5$ cells/ml/well (1 ml RPMI 1640 culture medium per well), and incubated overnight at 37° C. in 5% $CO_2$/air.
3. The following day, the solutions from step 1 were administered to wells containing cells in step 2, to give three wells each with a final concentration of 12.5 ug/ml of peptide. Additional wells containing cyclodextrin alone at 62.5 ug/ml were also prepared. The remaining wells were left untreated. The plate was incubated for a further four hours at 37 degC.
4. Lipopolysaccharide (from *E. coli* strain 0111 B4) was added to the wells receiving the cyclic oligopeptide solution, as well as three of the wells receiving no peptide. The final concentration of lipopolysaccharide was 0.1 ug/ml.
5. The plate was incubated overnight, and the following day the supernatants were assayed for TNF using a commercial ELISA kit.

| Peptide (12.5 ug/ml) | LPS | TNF concentration (pg/ml) | Standard deviation |
|---|---|---|---|
| cyclo(-A-K-Σ-Y-E-K-A-Σ-E-Y) | + | 486.9 | 33.5 |
| cyclo(-A-K-Σ-E-Y-K-A-Σ-Y-E) | + | 928.8 | 72.7 |
| Cyclodextrin alone | + | 622.3 | 22.9 |
| Medium + LPS | + | 637.6 | 26.0 |
| Medium control | − | 50.8 | 9.0 |

Results obtained, shown in the table, demonstrate that one, but not both, of the cyclic oligopeptides tested have an effect in suppressing TNF secretion stimulated by LPS. Accordingly, the sequence of the amino acids in each domain has an effect on the biological activity of the oligopeptide. Cyclo(-A-K-Σ-Y-E-K-A-Σ-E-Y) will be useful in treatment of multiple sclerosis, since it comprises the same amino acids (except in a non-random configuration) as Copaxone and displays the same effect on TNF secretion by macrophages.

Example 7

Inhibition of Enzyme Activity of Thrombin

1. Cyclic oligopeptides of the following structures were synthesised as previously described, and prepared in complexed form with cyclodextrin at concentration of 1 mg/ml on Hanks Balanced Salts Solution using the procedure outlined in example 6.

(i) cyclo(-R-E-Σ-S-R-E-R-Σ-S-E-)

(ii) cyclo(-A-K-ΣE-Y-K-A-ΣY-E-)

(iii) cyclo(-dF-R-C-S-dF-R-C-S-)

(iv) cyclo(-dF-S-C-R-dF-S-C-R-)

All amino acids are in the L form unless indicated otherwise.

All amino acids are linked by peptide bonds.

Wherein R, E, S, Y, K and A represent the epitope-forming amino acids, Σ represents the associating functional group borne on the associating amino acid wherein the associating amino acid is an L-alpha aminocarboxylic acid and the associating functional group is a side-chain residue consisting of a straight aliphatic chain containing ten carbon atoms and C represents cysteine, wherein the cysteines in each ring are oxidised to form an internal bridge.

2. In wells of a 394-well microplate, 20 ul of thrombin solution (0.01 mg/ml) were dispensed, and mixed with 60 ul of cyclic oligopeptide solution 3. 20 ul of the substrate boc-beta-benzyl-Asp-Pro-Arg-7-amido-4-methylcoumarin hydrochloride (0.01 mg/ml) was added to each well, and the time course of generation of substrate was measured.

4. From the results shown in the table below it can be seen that the cyclic oligopeptides studied have differential effects in inhibiting thrombin proteolytic activity, and that these differential activities are related to the nature and combination of the amino acids included in the ring. It is clear that, with the correct choice of amino acids, structures based upon the constrained cyclic oligopeptide template can be created which are sufficiently rigid to exert significant effects on the activity of enzymes.

Accordingly, cyclic oligopeptides according to the present invention which have an effect inhibiting thrombin proteolytic activity may be used to treat diseases wherein protease activity is an exacerbating factor, including cardiovascular disease, circulation disorders and HIV.

| Time (minutes) | Control (enzyme alone) | Inhibition of Thrombin proteolytic activity (Fluorescence Units - Arbitrary Units) | | | |
|---|---|---|---|---|---|
| | | (i) | (ii) | (iii) | (iv) |
| 2.0 | 770.9 | 410.8 | 410.8 | 634.5 | 523.2 |
| 5.0 | 1821.1 | 816.4 | 816.4 | 1368.8 | 1205.3 |
| 10.0 | 2163.5 | 1189.4 | 1189.4 | 1786.9 | 1586.9 |
| 15.0 | 2253.2 | 1398.6 | 1398.6 | 1980.7 | 1751.7 |
| 20.0 | 2345.8 | 1592.1 | 1592.1 | 2107.4 | 1843.1 |
| 25.0 | 2359.0 | 1673.2 | 1673.2 | 2159.7 | 1864.8 |

It can be seen from the table that some cyclic oligopeptides had greater activity than others depending upon the order of amino acids in each domain.

Example 8

Suppression of TNF Secretion by Cyclic Oligopeptides Containing Two Different Epitopes 1. Two cyclic oligopeptides were prepared with the following structures:

(i) cyclo(-dF-S-Σ-Q-dL-S-Σ-R-)

and (ii) cyclo(-dF-S-Σ-L-dQ-S-Σ-R)

All amino acids are in the L form unless indicated otherwise.

All amino acids are linked by peptide bonds.

wherein Q, L, S, R and F represent the epitope-forming amino acids and Σ represents the associating functional group borne on the associating amino acid wherein the associating amino acid is an L-alpha aminocarboxylic acid and the associating functional group is a side-chain residue consisting of a straight aliphatic chain containing ten carbon atoms.

These cyclic oligopeptides were prepared as solutions in transcutol/cyclodextrin, as described in example 4, to give a final concentration of peptide of 1 mg/ml, and cyclodextrin at 20 mg/ml.

2. J774A.1 cells (a macrophage cell line) were plated out in all the wells of three 24-well cluster plates at a seeding density of $3 \times 10^5$ cells/ml/well (1 ml RPMI 1640 culture medium per well), and incubated overnight at 37° C. in 5% $CO_2$/air.

3. The following day, the solutions from step 1 were administered to wells containing cells in step 2, to give three wells each with a final concentration of 50, 25, 12.5, 6.25 or 3.125 ug/ml of cyclic oligopeptide. Additional wells containing cyclodextrin at 1, 0.5, 0.25, 0.125 and 0.0625 mg/ml were also prepared. The remaining wells were left untreated. The plate was incubated for a further four hours at 37 degC.

4. Lipopolysaccharide (from *E. coli* strain 0111 B4) was added to the wells receiving the octapeptide solution, as well as three of the wells receiving no peptide. The final concentration of lipopolysaccharide was 0.1 ug/ml.

5. The plate was incubated overnight, and the following day the supernatants were assayed for TNF using a commercial ELISA kit.

Results obtained, shown in the table below, demonstrate that cyclic oligopeptides containing two non-identical epitopes, of which one is comprised of F, R and S amino acids, are able to down-regulate the secretion of TNF from J774 cells in a dose-dependent manner.

| Peptide conc. | Medium | TNF concentration (pg/ml) | | |
|---|---|---|---|---|
| (ug/ml) | control | (i) | (ii) | Cyclodextrin |
| 0 | 27 + 3 | 2856* | 2856* | 2856* |
| 3.125 | | 2856* | 2648 ± 43 | 2856* |
| 6.25 | | 2460 ± 83 | 2325 ± 67 | 2856* |
| 12.5 | | 1595 ± 64 | 1748 ± 20 | 2856* |
| 25 | | 1341 ± 50 | 1437 ± 85 | 2376 ± 21 |
| 50 | | 843 ± 42 | 1081 ± 142 | 2225 ± 51 |

*Readings higher than the maximum detectable limit

The invention claimed is:

1. An internally-constrained cyclic oligopeptide comprising a ring of ten amino acids for specifically binding to a target ligand, wherein the ring comprises two amino acid domains, each domain comprising four epitope-forming amino acids, and two associating functional groups positioned so that they form one or more intra-cyclic non-covalent associations; whereby the cyclic oligopeptide is constrained in a single conformation so that the epitope-forming amino acids form an epitope in each domain, each epitope being capable of specifically binding to a target ligand, wherein the cyclic oligopeptide has the following structure:

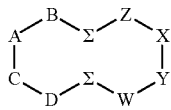

wherein A, B, C, D, W, X, Y and Z represent the epitope-forming amino acids; one epitope is formed from the domain D-C-A-B and one epitope is formed from the domain Z-X-Y-W; and the Z-X-Y-W domain and/or the D-C-A-B domain is selected from the group consisting of YEKA (SEQ ID NO: 1), YEAK (SEQ ID NO: 2), YAKE (SEQ ID NO: 3), YAEK (SEQ ID NO: 4), YKAE (SEQ ID NO: 5), YKEA (SEQ ID NO: 6), EYKA (SEQ ID NO: 7), EYAK (SEQ ID NO: 8), EKAY (SEQ ID NO: 9), EKYA (SEQ ID NO: 10), EAKY (SEQ ID NO: 11), EAYK (SEQ ID NO: 12), KAYE, (SEQ ID NO: 13) KAEY (SEQ ID NO: 14), KYAE (SEQ ID NO: 15), KYEA (SEQ ID NO: 16), KEAY (SEQ ID NO: 17), KEYA (SEQ ID NO: 18), AKEY (SEQ ID NO: 19), AKYE (SEQ ID NO: 20), AYEK (SEQ ID NO: 21), AYKE (SEQ ID NO: 22), AEYK (SEQ ID NO: 23) and AEKY (SEQ ID NO: 24); and each Σ is a lipidic amino acid with a linear hydrocarbon side chain associating functional group comprising a hydrocarbon chain between 8 and 20 carbons in length.

2. The cyclic oligopeptide according to claim 1, wherein each epitope-forming amino acid adjacent to an associating functional group has the same stereochemical configuration as the adjacent associating functional group.

3. The cyclic oligopeptide according to claim 1, wherein the epitopes are the same.

4. The cyclic oligopeptide according to claim 1, wherein the linear hydrocarbon side chain is a $C_{10}$-C16 linear hydrocarbon side chain.

5. The cyclic oligopeptide according to claim 1, wherein the Z-X-Y-W domain is YEKA (SEQ ID NO: 1) and the D-C-A-B domain is EYAK (SEQ ID NO: 8).

6. A method for producing the cyclic oligopeptide of claim 1 for specifically binding to a target ligand comprising:
   i) providing the epitope-forming amino acids;
   ii) producing a cyclic oligopeptide incorporating the epitope-forming amino acids.

7. The method according to claim 6, wherein the step of providing the epitope-forming amino acids comprises
   (a) selecting a set of conjugates, each conjugate comprising a head group and a tail group, with an array of head groups, wherein each head group comprises an amino acid;
   (b) forming a non-covalent association therefrom, in which the tail groups aggregate hydrophobically and in which the conjugates are movable;
   (c) assaying for sufficient interaction between the noncovalent association and the target ligand;
   (d) optionally repeating steps (a) to (c) using a set of conjugates with a modified array of head groups; and
   (e) on finding sufficient interaction in step (c) selecting the amino acids of the head groups of the set of conjugates as the epitope-forming amino acids in step (a).

* * * * *

SEQUENCE LISTING

<160> NUMBER OF SEQ ID NOS: 26

<210> SEQ ID NO 1
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 1

Tyr Glu Lys Ala
1

<210> SEQ ID NO 2
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 2

Tyr Glu Ala Lys
1

<210> SEQ ID NO 3
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 3

Tyr Ala Lys Glu
1

<210> SEQ ID NO 4
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 4

Tyr Ala Glu Lys
1

<210> SEQ ID NO 5
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 5

Tyr Lys Ala Glu
1

<210> SEQ ID NO 6
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 6

Tyr Lys Glu Ala
1

```
<210> SEQ ID NO 7
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 7

Glu Tyr Lys Ala
1

<210> SEQ ID NO 8
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 8

Glu Tyr Ala Lys
1

<210> SEQ ID NO 9
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 9

Glu Lys Ala Tyr
1

<210> SEQ ID NO 10
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 10

Glu Lys Tyr Ala
1

<210> SEQ ID NO 11
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 11

Glu Ala Lys Tyr
1

<210> SEQ ID NO 12
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 12

Glu Ala Tyr Lys
1
```

```
<210> SEQ ID NO 13
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 13

Lys Ala Tyr Glu
1

<210> SEQ ID NO 14
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 14

Lys Ala Glu Tyr
1

<210> SEQ ID NO 15
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 15

Lys Tyr Ala Glu
1

<210> SEQ ID NO 16
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 16

Lys Tyr Glu Ala
1

<210> SEQ ID NO 17
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 17

Lys Glu Ala Tyr
1

<210> SEQ ID NO 18
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 18

Lys Glu Tyr Ala
1
```

```
<210> SEQ ID NO 19
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 19

Ala Lys Glu Tyr
1

<210> SEQ ID NO 20
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 20

Ala Lys Tyr Glu
1

<210> SEQ ID NO 21
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 21

Ala Tyr Glu Lys
1

<210> SEQ ID NO 22
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 22

Ala Tyr Lys Glu
1

<210> SEQ ID NO 23
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 23

Ala Glu Tyr Lys
1

<210> SEQ ID NO 24
<211> LENGTH: 4
<212> TYPE: PRT
<213> ORGANISM: ARTIFICIAL SEQUENCE
<220> FEATURE:
<223> OTHER INFORMATION: D-C-A-B domain sequence

<400> SEQUENCE: 24

Ala Glu Lys Tyr
1

<210> SEQ ID NO 25
```

```
<211> LENGTH: 4
<212> TYPE: PRT
<213> ORGANISM: ARTIFICIAL SEQUENCE
<220> FEATURE:
<223> OTHER INFORMATION: Epitope-forming amino acids

<400> SEQUENCE: 25

Ser Arg Glu Arg
1

<210> SEQ ID NO 26
<211> LENGTH: 4
<212> TYPE: PRT
<213> ORGANISM: ARTIFICIAL SEQUENCE
<220> FEATURE:
<223> OTHER INFORMATION: Epitope-forming amino acids

<400> SEQUENCE: 26

Ser Glu Arg Glu
1
```